United States Patent [19]

Harris

[11] Patent Number: 5,197,947

[45] Date of Patent: Mar. 30, 1993

[54] POWERED CLYSIS AND CLYSER

[75] Inventor: Vaughn Harris, Albuquerque, N. Mex.

[73] Assignee: University of New Mexico, Albuquerque, N. Mex.

[21] Appl. No.: 780,991

[22] Filed: Oct. 24, 1991

[51] Int. Cl.⁵ .......................................... A61B 10/00
[52] U.S. Cl. ........................................ 604/28; 604/22; 604/51
[58] Field of Search .................. 604/22, 48, 43, 28, 604/49, 51

[56] References Cited

U.S. PATENT DOCUMENTS

| | | | |
|---|---|---|---|
| 1,112,107 | 9/1914 | Anderson. | |
| 3,033,194 | 5/1962 | Lippert | 604/22 |
| 3,805,793 | 4/1974 | Wright | 604/22 |
| 3,902,495 | 9/1975 | Weiss et al. | 604/22 |
| 4,136,700 | 1/1979 | Broadwin et al. | 604/22 |
| 4,413,987 | 11/1983 | Schwartz. | |
| 4,496,342 | 1/1985 | Banko | 604/22 |
| 4,578,059 | 3/1986 | Fabricant et al. | 604/43 |
| 4,634,420 | 1/1987 | Spinosa et al. | 604/22 |
| 4,705,038 | 11/1987 | Sjostrom et al. | 604/22 |
| 4,813,927 | 3/1989 | Morris et al. | 604/48 |
| 4,895,561 | 1/1990 | Mahurkar | 604/43 |
| 4,898,574 | 2/1990 | Uchiyama et al. | 604/22 |
| 4,913,698 | 4/1990 | Ito | 604/22 |

Primary Examiner—Paul J. Hirsch
Attorney, Agent, or Firm—Hoffman, Wasson & Gitler

[57] ABSTRACT

A pneumatically powered clysis device which can be rapidly assembled from disposable components. The device allows the rapid infusion of subcutaneous fluids to greatly facilitate the harvesting of grafts from the abdomen, chest, back and head.

4 Claims, 1 Drawing Sheet

POWERED CLYSIS AND CLYSER

BACKGROUND OF THE INVENTION

This invention relates to clysis, or the rapid infusion of a subcutaneous fluid. Clysis is a commonly used method to facilitate the harvesting of skin grafts over bony prominences such as the rib cage, spine, tibia and skull.

The method is helpful in loose surfaces such as the abdomen to produce an even skin tension and minimize hang up of the dermatome both in graft harvesting and eschar debridement.

Additionally, clysis has been utilized for the introduction of antibiotics into the subeschar space.

Most commonly, clysis is performed with a manually powered syringe and an attached one-way valve (Pitkin syringe). This type of process is slow and tiring when large volumes of fluid are infused.

SUMMARY OF THE INVENTION

It is an object of the present invention to provide a method for the rapid infusion of a subcutaneous fluid which overcomes the tediousness of the prior manual syringe process as well as a unique product for performing the process.

It is an object of the present invention to provide a method for the rapid infusion of a subcutaneous fluid which utilizes a pneumatically driven apparatus composed of disposable instruments.

A further object of the present invention is to provide a pneumatically powered clysis device which performs faster and easier than the conventional Pitkin syringe.

A further object of the present invention is to provide a pneumatically powered clysis device which facilitates the harvesting of grafts from the abdomen, back and head, especially when long uniform split thickness grafts are required.

A further object of this invention is to provide a pneumatic process for harvesting skin for grafts. Infiltrate is pneumatically and rapidly pumped through a tube and then infused via a spinal needle into a desired subcutaneous area.

The present inventive method utilizes sterile disposable components. The main power source is a pneumatic pulse lavage. A conventional shower head tip is opened at one end and the opened tubing is used in conjunction with a three-way stopcock to connect the power source to extension tubing. To the other end of the extension tubing there is attached a Luer-Lock adapter which facilitates connection of a spinal needle.

Once the pulse lavage is connected to compressed air and infiltrate of choice, the system is primed. A desired air pressure is selected and the needle is inserted through the skin into the subcutaneous space. By manipulation of the needle within the tissues a large area can be treated in a short time.

DETAILED DESCRIPTION OF THE PREFERRED EMBODIMENT

Figure 1:
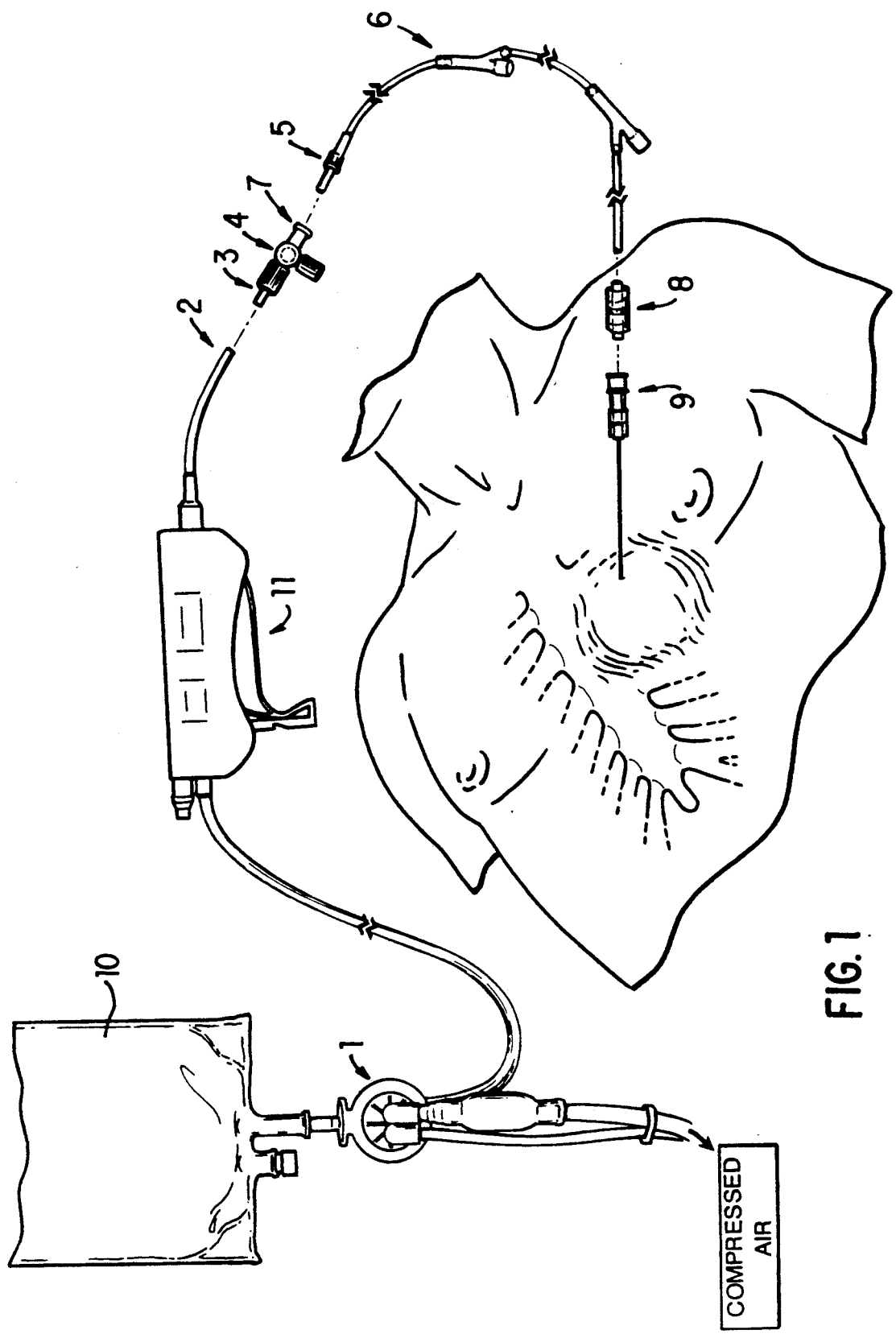
FIG. 1 is a view illustrating the invention.

The flexible and easy to operate injection system is rapidly fabricated from available sterile disposable components. The main power source is a pneumatic pulse lavage 1. The pneumatic pulse lavage conventionally is utilized for wound irrigation. Handle 13 is compressed and when released the flow of fluid emanating from 10 is fed through the system ultimately reaching the tissue area. A shower head tip is removed and created is an open end 2 that easily accommodates the male end 3 of a three-way stopcock 4 for attachment to the lavage 1. The three way stopcock 4 is a device often utilized in intravenous set-ups where more than one bag of fluid is to be infused. One port 12 is closed off. The male end 5 of extension tubing 6 is attached to the female port 7 of the three-way stopcock 4. The tubing 6 is used for lengthening or extending the intravenous line. To the other end of the extension tubing 6, a double male-ended Luer-Lock adaptor 8 is attached. The double male ended Luer-lock 8 facilitates attachment of the extension tubing to the needle. A spinal needle 9 attached to the other end of the Luer-Lock adaptor 8 completes the set up.

The apparatus makes use of a compressed air source and an infiltrate 10, of choice. Compressed air sources are available in most hospital settings or from compressed air tanks.

Once all the components are connected, the apparatus is primed by squeezing the handle 11 and allowing the flow of infiltrate to be fed into the lavage. The three-way stopcock 4 and all extension tubing 6 turn screws are turned to their open positions. A desired air pressure is selected, usually between 60 and 80 psi, and maintained. A selected needle 9, preferably 18 gauge, is inserted through the skin into the subcutaneous space. The needle's large bore facilitates a large flow of fluid and the extended length of the needle allows for desired deep penetration into tissues. By squeezing the handle 11, one can easily and rapidly infuse as much infiltrate 10 as is required for a given area. By manipulation of the needle 9 within the tissues, a large area can be treated in a short time.

The system can infuse infiltrates such as saline at a rate of 300 cc per minute for an indefinite period of time. This is far superior to the existing manual process which at best can deliver 170 cc per minute, followed by manual fatigue.

The invention utilizes the structure above for a unique method for harvesting skin for grafts.

Various modifications and alterations of this system and apparatus will become apparent to those skilled in the art without departing from the scope and spirit of this invention, and it should be understood that this invention is not unduly limited to the illustrative embodiment set forth herein.

What is claimed is:

1. A method for harvesting skin for grafts comprising the steps of:
   (a) rapidly and pneumatically pumping an infiltrate through a tube; and
   (b) infusing said infiltrate into a desired subcutaneous area, wherein said infiltrate is rapidly and pneumatically pumped through a tube and infused into a desired subcutaneous area via a sterile disposable injection system comprising:
      (1) a pneumatic pulse lavage;
      (2) a three-way stopcock connected to said lavage;
      (3) extension tubing connecting said stopcock to a Luer-Lock adaptor; and
      (4) a spinal needle connected to said Luer-Lock adaptor for insertion into a desired area for infusing a desired infiltrate therein.

2. A method in accordance with claim 1, wherein said pneumatic pulse lavage further comprises a compressed air power source.

3. A method in accordance with claim 2, wherein said compresses air power source delivers from 60 to 80 psi.

4. A method in accordance with claim 1, further comprising the steps of:

(c) priming the system by starting a flow of a selected infiltrate therethrough;
(d) opening all valves in the system;
(e) inserting the needle into a desired tissue location; and
(f) manipulating said needle within said tissue thereby treating the area with said fluid.

* * * * *